United States Patent [19]

Phadke et al.

[11] Patent Number: 5,266,334
[45] Date of Patent: Nov. 30, 1993

[54] SUGAR-FREE DRY MIX CELLULOSE ETHER COMPOSITIONS AS BULK LAXATIVES

[75] Inventors: Deepak S. Phadke, Olathe, Kans.; Julie L. Collier, Indianapolis, Ind.

[73] Assignee: Merrell Dow Pharmaceuticals Inc., Cincinnati, Ohio

[21] Appl. No.: 922,130

[22] Filed: Jul. 29, 1992

[51] Int. Cl.$^5$ .................. A61K 9/14; A61K 31/70
[52] U.S. Cl. ..................... 424/489; 424/439; 424/499; 514/57; 514/777; 514/892; 514/911; 426/804
[58] Field of Search ............... 424/439, 489; 514/781, 514/892, 911, 57, 777

[56] References Cited

U.S. PATENT DOCUMENTS

| | | | |
|---|---|---|---|
| 4,671,823 | 6/1987 | Shah et al. | 106/197 |
| 5,137,716 | 8/1992 | Weisenfeld | 514/911 |
| 5,143,728 | 9/1992 | Cappel et al. | 514/892 |

*Primary Examiner*—Thurman K. Page
*Assistant Examiner*—James M. Spear
*Attorney, Agent, or Firm*—Michael J. Sayles

[57] ABSTRACT

Water-dispersible sugar-free powdered, bulk laxative compositions containing cellulose ethers as the active agent are disclosed. These bulk laxative compositions form smooth, palatable dispersions in water which dispersions contain a therapeutically effective amount of the cellulose ether.

4 Claims, No Drawings

SUGAR-FREE DRY MIX CELLULOSE ETHER COMPOSITIONS AS BULK LAXATIVES

BACKGROUND OF THE INVENTION

This invention relates to sugar-free, dry mix cellulose ether bulk laxative compositions.

It has been long known that cellulose ethers, such as carboxymethylcellulose and methylcellulose are effective bulk laxatives. The cellulose ethers relieve constipation by increasing the bulk of the stool, increasing the water content of the stool, and it is believed, by a lubricating effect on the stool.

Previously, cellulose ethers have been administered as bulk laxatives in the form of tablets, powders, and suspensions in highly concentrated sugar solutions. Each of these methods of administration has significant disadvantages which have limited the acceptance of these products by consumers.

Tableted cellulose ethers, for example, do not readily dissolve in the digestive tract because these cellulose ethers are highly hygroscopic. The outer portion of the tablet quickly forms a gel-like hydrate which prevents break up of the tablet and greatly retards hydration of the interior portions of the tablet. Accordingly, the tablet is often excreted as an intact soft gel mass. Although some laxative effect is produced by such gel masses, the cellulose ether is most effective when dispersed uniformly throughout the stool. Thus, when employed in tablet form, cellulose ethers have reduced efficacy as bulk laxatives.

Cellulose ethers have also been administered as powders, which powders are swallowed by the patient. Such powders often exhibit the same type of gelation as tablets, i.e., the individual particles lump together and remain partially undissolved as they pass through the digestive tract. Moreover, administration of cellulose ethers in powder form has caused nausea, cramping, and vomiting in some patients. Accordingly, cellulose ethers are not advantageously administered in powder form.

Cellulose ethers have also been administered as bulk laxatives as suspensions of the cellulose ether in water containing high concentrations of sucrose or other sugars and a flavoring. The sugar competes with the cellulose ether for the available water, thereby preventing the cellulose ether from hydrating sufficiently to form gels. The administration of cellulose ethers in such form has the advantage that the cellulose ether is sufficiently dispersed that it does not form significant amounts of lumps in the digestive tract. Unfortunately, however, such suspensions are very thick and semi-gelatinous. As such, they are visually unappealing. More significantly, due to their slimy mouth feel and extreme sweetness, such suspensions are quite unpalatable. Accordingly, such cellulose ether suspensions have not gained significant consumer acceptance.

Accordingly, a cellulose ether composition useful as a bulk laxative, which composition is palatable and not visually displeasing and which is administered without the formation of significant amounts of lumps or gels was developed.

Citrucel ® Orange, a bulk forming laxative containing methylcellulose as its active ingredient, was first introduced into the market in 1986. This product contains 15 g of sucrose in the 19 g adult dose which corresponds to a 2 g dose of methylcellulose. To reduce the high sugar content of this product, a natural flavor formula lower in caloric content and containing only 1 g of sucrose was developed and introduced as a line extension in 1988. However, it was still desirable to produce a sugar-free bulk laxative composition, which is essentially sugar-free and thus virtually calorie free (it will be noted that the dispersing agent used herein, namely maltodextrin, has a few calories, namely 4 calories per gram). A major problem in doing so, however, was that the sugar component acted not only as a sweetening agent, but also as a dispersing agent as well.

SUMMARY OF THE INVENTION

The present invention is such a sugar-free, bulk laxative composition. This invention is a particulate bulk laxative composition comprising a dry mixture of (a) an edible, water-soluble cellulose ether having efficacy as a bulk laxative (b) a sugar-free sweetening component and (c) a dispersing agent. The relative proportions of the cellulose ether and the dispersing agent and the sweetening component are chosen together such that a quantity of the bulk laxative composition having a therapeutically effective dose of the cellulose ether contains sufficient amounts of a dispersing composition that upon mixture thereof in about 4-16 ounces of cold water with mild agitation, a smooth mixture is formed which does not contain significant amounts of gels or lumps.

In order to achieve a smooth mixture which does not contain significant amounts of gels or lumps, the relative proportions of the cellulose ether, the dispersing agent and the sweetening agent are in the ratio of 15-25:45-55:1 by weight. More preferably, the ratio is approximately 20:50:1 by weight.

It has been found that when the bulk laxative compositions of this invention are mixed with the aforementioned amount of water the resulting mixture is palatable and smooth without substantial amounts of lumps or gels, and, when ingested by the patient, delivers a therapeutically effective dose of the cellulose ether. In addition, to add flavor, an orange flavor base has been added. Because such mixtures containing the bulk laxative compositions of this invention are palatable, patients are more likely to take these laxatives regularly as prescribed. Furthermore, because of the uniform dispersion of the cellulose ether in the water, the cellulose ether is administered in the form in which it is more effectively employed.

An additional advantage of the bulk laxatives of this invention is that ordinary administration thereof causes the patient to ingest significant quantities of fluids. Such simultaneous ingestion of fluids is generally recognized as necessary for proper functioning of a bulk laxative.

DETAILED DESCRIPTION OF THE INVENTION

The cellulose ether employed herein is any water-soluble cellulose ether which is effective as an active agent in a bulk laxative. By "effective as an active agent in a bulk laxative" is meant that the cellulose ether measurably increases the bulk, water content, and/or the frequency of the stools of patients to which it is administered. Such cellulose ethers include, for example, sodium carboxymethylcellulose, methylcellulose, hydroxypropylmethylcellulose, hydroxyethylmethylcellulose, hydroxypropylcellulose, hydroxyethylcellulose, and the like. The particular substituent and amount of substitution is not particularly critical as long as the resulting cellulose ether is edible, water-soluble, and effective as an active agent in a bulk laxative. However, this invention is particularly useful when the cellulose ether is one which is soluble but poorly dispersible in water, such as carboxymethylcellulose, or which is soluble, poorly dispersible in cold water but readily dispersible in hot water, such as methylcellulose or hydroxypropylmethylcellulose. The molecular weight of the cellulose ether is not especially critical.

Because an effective dose of the cellulose ether may be administered in either a single application or a plurality of applications, for the purposes of this invention, a therapeutically effective amount of the cellulose ether is considered to be from about 0.25 to about 8, preferably about 1 to about 4, grams of the cellulose ether per administration. Of course, the effective amount of cellulose ether may vary somewhat depending on factors such as the size, age, and sex of the patient, and the severity of the problem to be treated. Since multiple doses of the bulk laxatives are commonly and often advantageously administered to the patient, relatively small amounts, i.e., about 0.25 to about 3 grams of the cellulose ether may be taken in each dose. However, larger amounts of the cellulose ether may be contained in a dose if only a single daily dose of the bulk laxative is to be taken. When less than about 0.25 gram of the cellulose ether is taken in a single dose, the large number of doses required to administer a therapeutically effective amount of the cellulose ether tends to lead to poor patient compliance. Ingestion of large amounts of the cellulose ether (i.e., above about 8 grams per dose) generally does not increase the efficacy of the cellulose ether and is therefore not preferred.

The cellulose ether is present in the bulk laxative compositions of this invention in a particulate form, such that the cellulose ether can be readily dispersed in water without the formation of significant amounts of gels, lumps, and the like. Generally, the particles are of a size such that upon contact with water, hydration of the interior regions of the particle occurs in a short period of time, i.e., one minute or less. Preferably, the cellulose ether is in the form of a powder having a volume average particle diameter of less than about 400, preferably less than 250, microns.

A sugar-free sweetening component, preferably aspartame, is also employed in the bulk laxative composition of this invention to sweeten aqueous dispersions containing the bulk laxative. Since sugar usually acts as a dispersing agent as well as a sweetener and since aspartame does not perform well as a dispersing agent, a dispersing agent had to be found which facilitated dispersion of the cellulose ether into solution.

The type and amount of said dispersing agent is chosen such that the resulting bulk laxative composition is a particulate solid which is readily dispersed in about 4–16 ounces of cold water, forming an edible, palatable dispersion containing a therapeutically effective amount of the cellulose ether.

While said dispersing agent may be inert, i.e., not substantially contributing to the taste or efficacy of the bulk laxative composition, it is desirable to employ as such agent substances which themselves contribute to the flavor, texture, and/or efficacy of the bulk laxative composition. Examples of such additional ingredients include dry particulate materials such as dry egg solids, diverse dextrines, dry powdered milk, dry milk solids, starches, modified or pregelatinized starch, tapioca starch, and the like. Of course, the particular choice of additional ingredient depends on the taste and texture desired in the dispersed bulk laxative composition.

In addition to the foregoing, the bulk laxative compositions of this invention optionally, but preferably, comprise a small amount of a flavoring, such as strawberry, orange, grape, raspberry, lemon, lime, cherry, licorice, spearmint, wintergreen, chocolate, eggnog, butterscotch, vanilla, banana and the like. Such natural and artificial flavorings are well known. Citric acid is commonly employed in conjunction with fruit flavorings. The flavoring is generally present only as a minor component of the bulk laxative composition, generally, comprising less than about 5, preferably less than about 2, weight percent of the composition. Such flavoring can be incorporated into the dispersing composition, into the cellulose ether, or into the previously blended mixture of cellulose ether and dispersing composition.

In addition to the foregoing, other materials such as preservatives, buffers, coloring, anticaking agents, antioxidants, opacifiers, vitamins and minerals, setting agents, and the like which are commonly employed in food, beverage, or drug substances may be employed herein in conventional manner.

The bulk laxative compositions of this invention are prepared by simple admixture of the components. However, the order of addition of components is not especially critical.

For the purposes of this invention, the bulk laxative composition is sufficiently dispersible if an amount thereof containing a therapeutically effective amount of the cellulose ether can be dispersed into 4–16 ounces of cold water without forming significant lumps or gels under the conditions of agitation provided either by spoon stirring or by an ordinary home mixer operated at low speed. Preferably, the composition can be dispersed by hand stirring to form a smooth, lump-free dispersion. "Cold" water, for the purposes of this invention, means water at a temperature below the cloud point of the cellulose ether employed in the bulk laxative composition, preferably at a temperature below about 30° C. When the cellulose ether employed does not exhibit a cloud point, cold water is taken to mean water having a temperature below 60° C., preferably below 30° C. "Cloud point," as that term is employed herein, means that temperature at which an aqueous solution containing 2 weight percent of the cellulose ether transmits 50 percent of the light transmitted by such solution at 20° C.

The bulk laxative compositions of this invention are employed by mixing an amount thereof which contains a therapeutically effective dose of the cellulose ether and about 4–16 ounces of water. After these compositions are dispersed in such liquid the resulting dispersion is then drunk by the patient. Mixtures of the bulk laxatives of this invention with water or other beverage are smooth, palatable, and essentially free of unpleasant gels and lumps.

As mentioned hereinbefore, the amount of the cellulose ether present in each dose, as well as the number of doses of the bulk laxative taken per day, will depend somewhat on the age, sex, size of the patient, severity of the patient's particular problem, the advice of the treating physician, if any, and the particular taste and habits of the patient. Accordingly, the bulk laxatives of this invention are advantageously administered in a single dose containing as much as about 8 grams of the cellulose ether, or in a plurality of small doses containing as little as 0.25 gram of the cellulose ether per dose. Most preferably, however, the bulk laxatives of this invention are taken as a single dose containing about 2-4 grams of the cellulose ether, or as two or more doses each containing about 1-3 grams of the cellulose ether.

The following example illustrates the invention but is not intended to limit the scope thereof. All parts and percentages are by weight unless otherwise indicated.

TABLE I

Orange Flavor Base, Sugar-Free Formula

| Ingredient | g/Dose | Formula (% w/w) |
|---|---|---|
| Aspartame | 0.092 | 1.278 |
| Orange Durarome SF #386552 | 0.720 | 10.00 |
| Orange Flavor 59.427 | 0.026 | 0.361 |
| Orange Flavor 59.432 | 0.059 | 0.819 |
| Potassium Citrate Granular | 0.324 | 4.500 |
| Calcium Phosphate Dibasic Anhydrous - FCC | 0.267 | 3.708 |
| Malic Acid | 0.700 | 9.722 |
| Riboflavin Type R | 0.005 | 0.0694 |
| Yellow FDC 6 Lake 40% | 0.007 | 0.0972 |
| Maltodextrin Agglomerated | 5.00 | 69.444 |
| TOTAL | 7.20 | 100.00 |

Manufacture of the Orange Flavor Base-SF is carried out in a two-step process as described below.

1. Preparation of the Premix

All flavor base ingredients, except for the maltodextrin, were added to the 42 cu. ft. Lodige mixer in the order listed (Table I). The contents were mixed for 3 minutes with the plow beds in operation but the choppers turned off. A 10 g sample was then taken from the top of the product bed through the side door of the Lodige and submitted for riboflavin and aspartame assays. The mixing process was continued for an additional 2 minutes under identical conditions, and an additional 10 g sample was taken for aspartame and riboflavin assays.

2. Addition of Maltodextrin

The 576.4 lbs. of Maltodextrin were then added and mixed for 1 minute with plows in operation but choppers off. A 100 g sample was taken from the top of the Lodige for aspartame and riboflavin assays and bulk and tapped density measurements. The contents were then mixed under the same conditions for an additional minute. Upon completion of mixing, 820 lbs. of the flavor base were discharged through a 10 mesh screen into a tote and 200 g samples were taken from the beginning, middle and end of discharge. Aspartame and riboflavin assays, sieve analysis, Karl Fischer and loss on drying moisture determinations, and bulk and tapped density measurements were performed.

TABLE II

CITRUCEL ® SUGAR FREE ORANGE FORMULA

| Ingredient | g/Dose | Percent w/w |
|---|---|---|
| CITRUCEL ® SUGAR FREE PREP | | |
| Methylcellulose | 2.000 | 19.608 |
| Maltodextrin 10DE | 1.000 | 9.804 |
| ORANGE FLAVOR BASE - SF | | |
| Orange Durarome SF #386552 | 0.720 | 7.059 |
| Potassium Citrate Granular | 0.324 | 3.176 |
| Aspartame | 0.092 | 0.902 |
| Orange Flavor 59.427 | 0.026 | 0.255 |
| Orange Flavor 59.432 | 0.059 | 0.578 |
| Riboflavin Type R | 0.005 | 0.0490 |
| Yellow FDC 6 Lake 40% | 0.007 | 0.0686 |
| Calcium Phosphate Dibasic Anhydrous - FCC | 0.267 | 2.618 |
| Malic Acid | 0.700 | 6.863 |
| Maltodextrin Agglomerated | 5.00 | 49.020 |
| TOTAL | 10.20 | 100.00 |

Final Product Blending

1. Preparation of the Citrucel ® Sugar Free Orange Final Blend

One 310 kg tote of Citrucel ® Sugar Free Prep (Table II) was charged through a security screen into the hopper which fed into the 75 cubic foot P-K blender. This was followed by two 372 kg totes of the Orange Flavor Base-SF. After closing the blender valve, the contents were mixed for 10 minutes and two 100 g samples were taken each from the top and bottom of the blender for methylcellulose, aspartame and riboflavin assays as well as bulk and tapped densities. The blender was then engaged for an additional 5 minutes to complete the blending process. Four 100 g samples were taken from the beginning, middle and end of discharge for a total of twelve discharge samples. Sieve analyses, physical characteristics, bulk and tapped densities, dispersion tests, and assays for aspartame, riboflavin, methylcellulose were performed on all samples. Loss on drying and Karl Fischer moisture tests, methylcellulose identity, and assays for methylcellulose on individual sieve cuts were performed on the middle samples only.

What is claimed is:

1. A particulate, sugar-free dry mix bulk laxative composition comprising (a) a water-soluble cellulose ether having efficacy as a bulk laxative, (b) a sweetening component consisting of aspartame and (c) a dispersing agent consisting of maltodextrin, wherein the relative proportions of the bulk laxative to the dispersing agent to the sweetening agent are 15-25:45-55:1 by weight such that upon mixture thereof with about 4-16 ounces of cold water with mild agitation, a dispersion is formed without significant amounts of gels and lumps.

2. A particulate, sugar-free dry mix bulk laxative composition according to claim 1 wherein the relative proportions of the bulk laxative to the dispersing agent to the sweetening agent are approximately 20:50:1 by weight.

3. A particulate, sugar-free dry mix bulk laxative composition according to claim 1 wherein the composition also includes an orange flavor base.

4. A particulate, sugar-free dry mix bulk laxative composition according to claim 2 wherein the composition also includes an orange flavor base.

* * * * *